United States Patent [19] [11] 3,991,360
Orth et al. [45] Nov. 9, 1976

[54] SENSOR ASSEMBLY FOR A HALOGEN GAS LEAK DETECTOR

[75] Inventors: Edward D. Orth, Boxford; John A. Roberts, Lynnfield, both of Mass.

[73] Assignee: General Electric Company, Schenectady, N.Y.

[22] Filed: May 16, 1975

[21] Appl. No.: 577,986

[52] U.S. Cl. .................................. 324/33; 73/19; 315/111
[51] Int. Cl.² ...................... G01N 27/62; H01J 7/24
[58] Field of Search ........... 324/33; 315/111, 111.9; 73/19, 23.1, 422 GC; 23/254 E

[56] References Cited
UNITED STATES PATENTS

| | | | |
|---|---|---|---|
| 2,652,532 | 9/1953 | Zemany | 324/33 |
| 3,439,262 | 4/1969 | Roberts | 324/33 |
| 3,471,746 | 10/1969 | Roberts | 315/111 |
| 3,683,272 | 8/1972 | Vissers et al. | 324/33 |

Primary Examiner—R. V. Rolinec
Assistant Examiner—Vincent J. Sunderdick
Attorney, Agent, or Firm—Vale P. Myles

[57] ABSTRACT

A sensor assembly for a halogen gas leak detector characterized by including a tubular, porous, high purity Alumina ($Al_2O_3$) element for supporting electrode and heater components in spaced-apart relationship relative to one another and a surrounding housing. The porous Alumina element is doped with an alkali metal by methods that cause the alkali metal to be distributed throughout the porous Alumina structure. The assembly is further characterized by incorporating a ribbon-like heater coil helically wound around the tubular Alumina element. In one embodiment of the invention the Alumina element is provided with a stepped end structure that effectively insulates the ends of an electrode mounted within the tubular element from the surrounding housing.

8 Claims, 6 Drawing Figures

GAS OUT

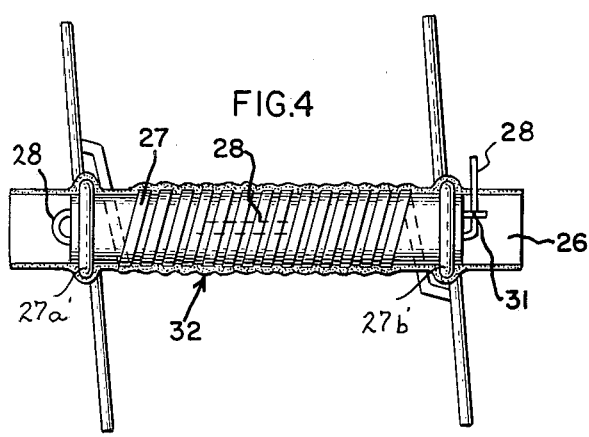

FIG.3

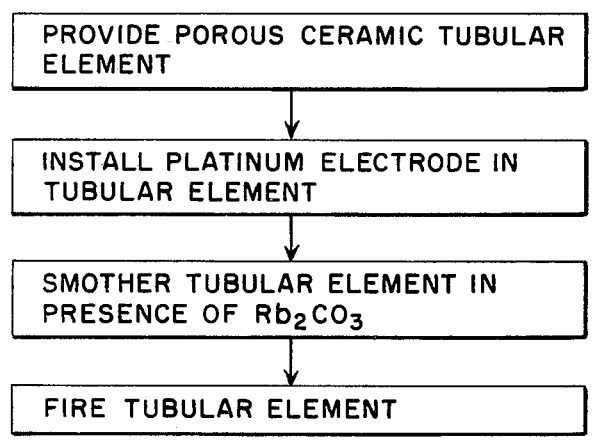

| PROVIDE POROUS CERAMIC TUBULAR ELEMENT |
| --- |
| ↓ |
| INSTALL PLATINUM ELECTRODE IN TUBULAR ELEMENT |
| ↓ |
| SMOTHER TUBULAR ELEMENT IN PRESENCE OF $Rb_2CO_3$ |
| ↓ |
| FIRE TUBULAR ELEMENT |

FIG.6

| PROVIDE POROUS CERAMIC TUBULAR ELEMENT |
| --- |
| ↓ |
| PROVIDE A DOPANT MIXTURE OF WATER AND $Na_2CO_3$ |
| ↓ |
| SOAK TUBULAR ELEMENT IN DOPANT IN A MOISTURE-TIGHT CONTAINER FOR AT LEAST 4 HOURS |
| ↓ |
| REMOVE TUBULAR ELEMENT FROM DOPANT AND BAKE FOR ABOUT 1 HOUR AT APPROXIMATELY 1225°C |

SENSOR ASSEMBLY FOR A HALOGEN GAS LEAK DETECTOR

BACKGROUND OF THE INVENTION

The invention is related to thermal chemical sensors of the type used to detect halogenated gas leaks, and more particularly, to a sensor assembly for a halogenated gas leak detector of a type that indicates the presence of halogen gas by producing a variation in electrical current between a pair of spaced-apart electrodes.

In the field of halogenated gas leak detectors it is common practice to position an alkali metal containing source, such as lithium, sodium, potassium, rubidium or cesium, in a thin platinum container which is heated by a separate platinum or platinum alloy heater coil. In leak detectors using such a sensor assembly, the air gap between the platinum container and the heater coil is typically biased with an electrical voltage of 150 to 300 volts and the heater coil is energized to raise its temperature to around 1,000° Centigrade. When thus energized, such a sensor will produce a background current of several microamperes between the heater anode and the platinum container. If the sensor is brought into contact with a halogenated gas, the current between the anode and platinum container increases in proportion to the concentration of halogen gas. Of course, other operating parameters such as the ambient temperature and magnitude of air flow through the sensor also have an effect on the amount of current flowing between the anode and platinum electrode of the sensor, but these parameters are easily compensated for, so such detectors have found wide commercial application. An example of one such prior art device is shown in U.S. Pat. No. 2,550,498—Rice which issued Apr. 24, 1951 and is assigned to General Electric Company.

When halogen gas detectors were first developed it was thought that an unimpeded air gap had to be maintained between the alkali metal containing central electrode and its associated surrounding anode heater. Relatively recent developments in the detector field have shown that the biasing electrode gap can, in fact, be substantially filled with ceramic material. See, for example, U.S. Pat. No. 2,806,991—White, issued Sept. 17, 1957 and assigned to General Electric Company. Moreover, it has been found that it is not necessary to position an alkali metal needed for effective operation of such sensors within the central electrode of a sensor assembly. At the same time, it is recognized that the normal use of such gas detectors requires a relatively rugged sensor assembly to successfully endure the mechanical vibration and shock that are encountered in ordinary use. As a practical matter, it is also necessary to provide a structure for such gas detector sensor assemblies that is commercially feasible to manufacture.

Prior art halogen gas leak detectors characteristically were relatively expensive to manufacture due in part to the use of complex spacing mechanisms needed to separate the alkali-containing central electrodes from the anode heater and due to the type of structure normally required to contain the alkali metal within the hollow platinum central electrode. Moreover, earlier gas leak detectors normally utilized round wire heating elements that were relatively expensive to manufacture and fairly inefficient in operation, and these prior art structures required larger amounts of platinum than are needed to practice the present invention.

Accordingly, it is a primary object of the present invention to provide a sensor assembly for a halogenated gas leak detector that overcomes the above-noted disadvantages of prior art leak detectors.

Another object of the invention is to provide a sensor assembly for a gas leak detector in which a helical heater coil is spaced from a central electrode by a porous ceramic element.

A further object of the invention is to provide a gas detector sensor assembly in which the thermal efficiency of a helical heater coil is improved relative to present day heater coils.

Yet another object of the invention is to provide an improved method for manufacturing a sensor assembly for a gas leak detector.

Additional objects and advantages of the invention will be apparent to those skilled in the art from the description of it presented herein.

SUMMARY OF THE INVENTION

In one preferred embodiment of the invention a sensor assembly for a halogen gas leak detector is formed of a porous ceramic tubular element having a relatively flat, ribbon-like heater anode coil wrapped snugly around it in a helical pattern. A platinum electrode is positioned substantially completely within the ceramic tubular element and is spaced from the heater anode by the ceramic wall of the element. The interstices of the porous ceramic element are doped with either sodium carbonate or rubidium carbonate. In a preferred form of the invention the respective ends of the tubular element are stepped orthogonally to insulate the ends of the platinum electrode from a surrounding housing. Preferred methods for applying the alkali metal dopant to the pores of the ceramic element include firing the element in the presence of alumina and rubidium carbonate in a pre-selected mixture and, alternatively, the tubular element can be submerged in a solution of sodium carbonate and water for a predetermined period of time after which the element is baked for about 1 hour at approximately 1225° Centigrade.

BRIEF DESCRIPTION OF THE DRAWINGS

FIG. 3 is a perspective view of a porous ceramic tubular element used in constructing one preferred form of the sensor assembly of the detector illustrated in FIG. 2.

FIG. 4 is a top plan view of an alternative embodiment of the sensor assembly for a detector such as that shown in FIG. 2. In this alternative embodiment, a heater anode coil and porous ceramic tubular element are at least partially encapsulated in a refractory cement coating.

FIG. 5 is a flow chart of a preferred method of manufacturing the sensor assembly for a gas leak detector constructed pursuant to the present invention.

FIG. 6 is another flow chart illustrating an alternative preferred method for manufacturing such a sensor assembly.

DESCRIPTION OF SOME PREFERRED EMBODIMENTS

Figure 1:
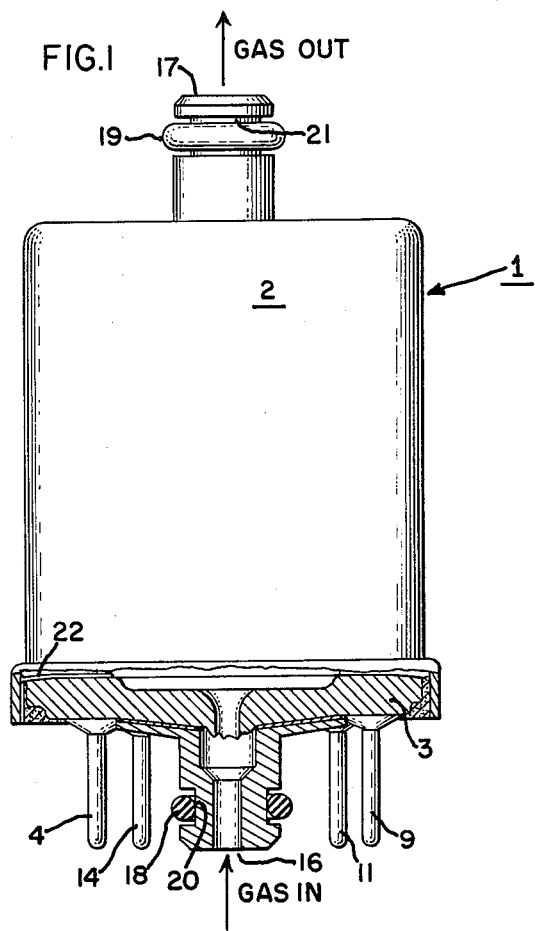
FIG. 1 is a side elevation view, partly in cross-section, of a halogen gas leak detector incorporating a sensor element constructed pursuant to the teaching of the present invention.

Referring to FIG. 1 it will be seen that there is shown a halogen gas leak detector 1 having an impervious cylindrical housing 2 mounted in sealing relationship to a base 3 that has 12 terminals (see FIG. 2) 4–15 mounted in a typical circular pattern thereon. As the description of the invention proceeds it will be apparent that various standard components may be used to form the foregoing parts of the gas detector of the present invention. For example, it will be obvious that a 12 terminal base member is not needed to form such a gas detector even though such a base member has been used in one preferred embodiment of the invention in order to employ relatively standard component parts.

The detector 1 also includes a gas inlet port 16, which extends through the base 3 into the interior of housing 2. In like manner, a gas exhaust port 17 is provided at the upper end of the detector 1 and extends through the top surface of the housing 2, so that in operation gas can flow into the port 16, through the housing 2, past a sensor assembly in the housing and then be exhausted from the housing 2 through the port 17. It is common practice in the gas detector field to provide removable fittings for the ports 16 and 17 so that they may be sealed when not in use or connected into an appropriate sampling system while in use. In order to secure such fittings (not shown) in position over the ports 16 and 17, a pair of rubber rings 18 and 19 are mounted respectively in annular grooves 20 and 21 formed in the outside of the tube means defining the inlet and outlet ports.

Figure 2:
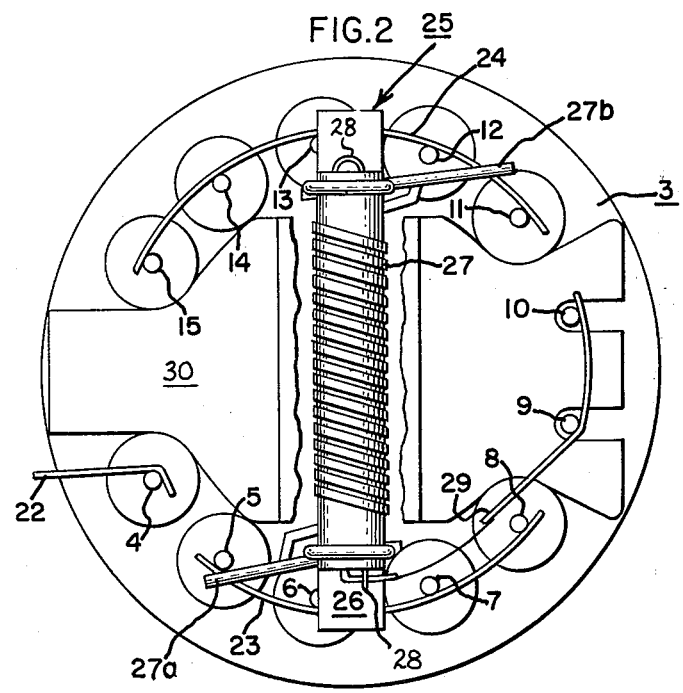
FIG. 2 is a top plan view of the detector shown in FIG. 1, with the covering housing of the detector removed to expose a sensor assembly of the detector, which is constructed pursuant to the teaching of the present invention.

As mentioned above, the foregoing components can be selected from a number of commercially available alternatives suitable for use in forming the basic halogen gas detector structure that is used in combination with the novel sensor assembly of the present invention, which will now be described in detail with reference to FIGS. 2 and 3 of the drawings. As seen in FIG. 2, the cover housing 2 of the detector 1 has been removed to expose to view the top of base 3 and the inner ends of terminals 4 through 15. A suitable electrical conductor 22 is attached by a resistance spot weld or other suitable method to the terminal 4 to provide a ground lead to the cover 2 (see FIG. 1) when the detector is assembled in operating form. Terminals 5 through 8 are electrically connected together using resistance spot welding by a common conductor 23 and terminals 11 through 15 are similarly connected in common by a conductor 24. Pursuant to the present invention, a sensor assembly 25 comprising a porous, doped, ceramic tubular element 26 (also seen in FIG. 3) and a helical anode heater coil 27 is mounted in a conventional manner on the base 3. An inner shield 30, used for directing the incoming gas over the sensor, is shown cut away for viewing the sensor assembly 25. The assembly 25 also includes a platinum hairpin electrode 28 (also see FIG. 3) that is positioned substantially completely within the parallel bores through tubular element 26, as best seen in FIGS. 3 and 4. As seen in FIG. 2, the platinum hairpin electrode 28 is electrically connected to a conductor 29 that serves as a terminal means and is resistance spot welded to the terminals 9 and 10 mounted on base 3. In order to hold the platinum electrode 28 firmly in position within the bores of tubular element 26 the hairpin is corrugated and the ends resistance spot welded or simply twisted together at 31. One external end of the corrugated hairpin is resistance spot welded to connector 29.

The opposite ends of the helical heater anode 27 are electrically connected, respectively, to the terminals 5 and 11 by suitable terminal means in the form of the lead ends 27a and 27b thereof which also provide a means for mounting the element assembly 25 by resistance spot welds to parts 23 and 24 shown in FIG. 2. Preferably, the heater element 27 is formed of platinum wire and in the disclosed preferred embodiment of the invention, the helical heater coil 27 is formed of flat platinum ribbon one side of which is snugly positioned over its entire length against the tubular element 26, in order to afford optimum heat exchange efficiency between the coil 27 and the tubular element 26. This novel construction affords a rugged durable heater anode structure that heats the tubular element 26 more uniformly, rapidly and efficiently than is possible with a conventional round wire anode. The platinum electrode positioned in the parallel tubular bores of the ceramic element 26 is of a hairpin design if a two hole tube is used as seen in FIGS. 3 and 4. In the preferred forms of the invention the porous alumina ceramic element 26 is doped with a dopant taken from the class including the carbonates of Rubidium, Sodium, Lithium, Potassium and Cesium. Such a dopant may be adequately dispersed and reacted in the interstices of the porous ceramic element 26 by the methods described in detail hereinafter. Before discussing those methods, reference will now be made to FIG. 4 of the drawings in order to describe a modification of the basic invention.

In FIG. 4 there is shown a tubular porous alumina ceramic element 26 having a ribbon-like platinum heater anode 27 would snugly thereon and having a hollow platinum electrode 28 positioned in the central bores thereof in exactly the same manner as such an assembly was described with reference to FIG. 2. To further improve the sensor assembly, a cured refractory cement coating 32 is disposed over substantially the entire helical heater coil 27 and the immediately juxtaposed portions of the tubular element 26 in order to secure the coil 27 in fixed position on the element 26. In leak detector applications where substantial vibration of the detector is anticipated such a cemented sensor assembly has been found to be particularly desirable in maintaining the thermal efficiency and electrical stability of the heater anode of the assembly.

Any suitable cement may be used to form the coating 32, but in the preferred embodiment of the invention the cement used is commercially available Norton cement (EA-139), which is a low silica cement that matures when fired at about 1300° Centigrade. The thickness of the cement coating 32 may vary between the range of 6/1000ths of an inch in the tube center to 3/100ths of an inch over the tube holders 27a' and 27b'. The refractory cement may be either brushed, dipped or sprayed into position. It has also been found desirable in some applications of the sensor assembly of the invention to continue the cement coating 32 over the ends of the platinum hairpin where it emerges from the tube (not so shown in FIG. 4) to securely lock the central electrode 28 in position within the tubular element 26.

A further important feature of the novel structure of the preferred embodiment of the invention is best described by reference to FIG. 3 of the drawings. As shown in FIG. 3, the tubular ceramic element 26 is provided with stepped end portions 26a and 26b that extend respectively substantially beyond the ends of the passageway through the tubular element in which the central electrode 28 is positioned. The purpose of the stepped portions 26a and 26b is to provide an insulating spacer between the outer housing 2 of the detector, the flexible conductor 29 and the opposite end of the central electrode 28. Such an insulating spaced arrangement relative to the housing 2 prevents the conductor 29 or the platinum electrode 28 from being shorted against the housing 2.

Although various porous ceramic materials may be used to form the tubular element 26, it has been found that a commercially available alumina material sold under the Tradename ALSIMAG No. 548 is suitably porous and rugged for the purposes of practicing the present invention. In order to sufficiently load the pores of the porous element 26 with an alkali metal pursuant to the preferred methods of the invention, two such preferred methods will now be described with reference to FIGS. 5 and 6. First, if it is desired to load the porous tubular element 26 with rubidium carbonate, the method shown in the flow diagram of FIG. 5 is suitable. Thus, to practice this method one first provides a porous ceramic tubular element formed of the above-noted alumina material or other suitable material. Next, in order to prevent the central passageway through the tubular element 26 from being plugged during a subsequent firing operation of platinum central electrode, such as the electrode 28, is installed within the passageway. After the platinum electrode has been installed in the tubular element 26 it is smothered in a powdered mixture of rubidium carbonate $Rb_2CO_3$ and alumina $Al_2O_3$ in which the rubidium carbonate is approximately ⅓ to approximately ½ by weight the weight of alumina. Preferably, the tubular element and the mixture of smothering material is loosely covered in a platinum dish, which is then placed in an oven and fired at about 1,000° Centigrade for 1 to 5 hours in order to sinter the $Rb_2CO_3$ throughout the pores of element 26. Following the firing operation the tubular element and central electrode are removed from the oven and platinum dish and allowed to cool, after which a helical coil heater anode such as the platinum ribbon 27 is applied thereto and the assembly may be mounted in a leak detector in the manner described above.

In an even more preferred method of applying alkali metal to the interstices of the porous tubular element 26, a fluid dopant is utilized in the manner that will now be described with reference to FIG. 6. Again, in practicing this method of manufacture, a suitable porous ceramic tubular element such as the element 26 is provided, and a dopant consisting essentially of between 85 and 65 percent by weight water and between 15 and 35 percent sodium carbonate ($Na_2CO_3$) is provided in a moisture tight bottle. Next, the tubular element is submerged in the dopant within the covered moisture tight bottle and gently agitated to remove entrapped air from the dopant. Such agitation is not essential and therefore the flow chart in FIG. 6 does not include this specific step; however, it has been found to be desirable in order to increase the efficiency of the operation. The tubular element is then allowed to soak in the dopant for at least 4 hours, after which it is removed from the bottle of dopant and placed in a loosely covered platinum container and baked in a furnace for about 1 hour at approximately 1200° Centigrade in order to remove substantially all of the moisture from the porous ceramic tubular element and leave the sodium carbonate dopant trapped and reacted in the pores of the element.

By using such loaded porous ceramic tubular elements a sensitive halogen gas leak detector can be made without having to load the central platinum electrode 28 with an alkali metal, as was normally required heretofore.

From the foregoing description of the invention it will be apparent to those skilled in the art that various modifications and improvements can be made in the invention based upon the teachings thereof presented above. Accordingly, it is my intention to encompass within the limits of the following claims the true spirit and scope of the invention.

What we claim and desire to secure by Letters Patent of the United States is:

1. A sensor assembly for a halogen gas leak detector comprising a porous doped ceramic tubular element, a helical heater coil wrapped snugly around said tubular element, and a platinum wire electrode positioned substantially completely within and supported by said tubular element, said tubular element being doped with a dopant taken from the class including carbonates of sodium, lithium, potassium, cesium and rubidium said coil and electrode being provided with terminal means for supplying a heating current through the coil and for applying a biasing voltage across the ceramic between the coil and electrode.

2. A sensor assembly as defined in claim 1 wherein the dopant is sodium carbonate.

3. A sensor assembly as defined in claim 2 wherein the helical heater coil is formed of flat platinum ribbon one side of which is snugly positioned against said tubular element.

4. A sensor assembly as defined in claim 3 including a cured refractory cement coating disposed over substantially the entire helical coil and the immediately juxtaposed portions of the tubular element to secure the coil in fixed position of the tubular element.

5. A sensor assembly as defined in claim 2 wherein said tubular element is formed of Alumina and has stepped end portions that extend respectively substantially beyond the ends of the passageway through the tubular element, and includes a pair of centrally disposed bores substantially parallel to the longitudinal axis of the element, said platinum wire electrode being formed of hairpin configuration with the legs thereof corrugated to resiliently engage portions of the sides of said bores thereby to retain the electrode in position within the bores.

6. A sensor assembly as defined in claim 1 wherein the doped ceramic tubular element is made by a method including the steps of:
   a. providing a porous high purity Alumina ($Al_2O_3$) tubular element,
   b. installing a platinum wire electrode in said tubular element,
   c. placing the tubular element in a platinum crucible and smothering the element with Alumina ($Al_2O_3$) powder that has been fired in the presence of rubidium carbonate ($Rb_2CO_3$) in a mixture containing about two parts by weight Alumina and one part by weight rubidium carbonate, and d. firing the tubular element at about 1000° Centigrade for 1 to 5 hours.

7. A sensor assembly as defined in claim 1 wherein the doped ceramic tubular element is made by a method including the steps of:
 a. providing a porous Alumina tubular element,
 b. providing a dopant consisting essentially of between 85 and 65 percent by weight water and between 15 and 35 percent by weight sodium carbonate,
 c. placing the tubular element in a moisture tight bottle and covering the tubular element with the dopant,
 d. gently agitating the bottle to remove entrapped air from the dopant,
 e. allowing the tubular element to soak in the dopant for at least 4 hours,
 f. removing the tubular element from the dopant bottle, placing it in a loosely covered platinum container and baking the tubular element in a furnace for about 1 hour at approximately 1225° C.

8. A sensor assembly as defined in claim 1 wherein the doped porous Alumina tubular element is made by a method including the steps of:
 a. providing a porous high purity Alumina ($Al_2O_3$) tubular element,
 b. installing a platinum wire electrode in said tubular element,
 c. placing the tubular element in a platinum crucible and smothering the element with Alumina ($Al_2O_3$) powder that has been fired in the presence of sodium carbonate ($Na_2CO_3$) in a mixture containing about two parts by weight Alumina and one part by weight sodium carbonate, and
 d. firing the tubular element at about 1000° Centigrade for 1 to 5 hours.

* * * * *